United States Patent
Zugris

(10) Patent No.: US 12,279,936 B1
(45) Date of Patent: Apr. 22, 2025

(54) WEARABLE ARTICLE FOR URINARY MALE INCONTINENCE

(71) Applicant: Daniel Zugris, McLean, VA (US)

(72) Inventor: Daniel Zugris, McLean, VA (US)

(*) Notice: Subject to any disclaimer, the term of this patent is extended or adjusted under 35 U.S.C. 154(b) by 0 days.

(21) Appl. No.: 17/741,866

(22) Filed: May 11, 2022

(51) Int. Cl.
| | |
|---|---|
| *A61F 13/471* | (2006.01) |
| *A61F 5/44* | (2006.01) |
| *A61F 5/453* | (2006.01) |
| *A61F 13/47* | (2006.01) |
| *A61F 13/537* | (2006.01) |
| *A61F 13/53* | (2006.01) |

(52) U.S. Cl.
CPC .......... *A61F 13/471* (2013.01); *A61F 5/4401* (2013.01); *A61F 5/453* (2013.01); *A61F 13/4704* (2013.01); *A61F 13/53708* (2013.01); *A61F 2013/530481* (2013.01)

(58) Field of Classification Search
CPC ...... A61F 13/471; A61F 5/4401; A61F 5/453; A61F 13/4704; A61F 13/53708; A61F 2013/530481; A61F 5/44; A61F 13/15; A61F 13/53409; A61F 5/458
See application file for complete search history.

(56) References Cited

U.S. PATENT DOCUMENTS

| | | | |
|---|---|---|---|
| 4,886,509 A | 12/1989 | Mattsson | |
| 5,074,853 A * | 12/1991 | Bryant | A61F 5/4401 604/385.19 |
| 6,105,174 A | 8/2000 | Nygren | |
| 6,129,719 A * | 10/2000 | Nozaki | A61F 13/471 604/385.01 |
| 6,197,011 B1 | 3/2001 | Freitas | |
| 6,209,142 B1 | 4/2001 | Mattsson | |
| 6,336,919 B1 | 1/2002 | Davis | |
| 6,416,500 B1 * | 7/2002 | Wada | A61F 13/4704 604/347 |
| 6,530,909 B1 | 3/2003 | Nozaki | |
| 6,569,135 B1 | 5/2003 | Mula | |
| 6,817,992 B1 | 11/2004 | Sassak et al. | |
| 6,910,137 B2 | 6/2005 | Liebenow et al. | |
| 8,702,667 B1 | 4/2014 | Johnson | |
| 8,986,271 B1 * | 3/2015 | Horne | A61F 5/4408 604/385.09 |
| 10,307,305 B1 * | 6/2019 | Hodges | A61F 13/471 |
| 10,406,039 B2 | 9/2019 | Villarreal | |
| 11,219,560 B2 | 1/2022 | Villarreal | |

(Continued)

FOREIGN PATENT DOCUMENTS

| | | | |
|---|---|---|---|
| JP | H0938126 A * | 2/1997 | |
| JP | 2008-23247 | 2/2008 | |
| WO | 99-33422 | 7/1999 | |

*Primary Examiner* — Sarah Al Hashimi
*Assistant Examiner* — Jihad Dakkak
(74) *Attorney, Agent, or Firm* — Mark F. Smith; Smith Brandenburg Ltd.

(57) ABSTRACT

A wearable article for urinary male incontinence that is effective for absorbing urine, that prevents or minimizes the likelihood that urine will contact the skin around the wearer's abdomen, that is relatively thin such that it is not apparent when worn under the pants of the individual and can be comfortably worn under the pants of the wearer, and allows the wearer to easily release the male member for urinating in a urinal or toilet and to easily place the male member back in position in the article.

20 Claims, 11 Drawing Sheets

(56) References Cited

U.S. PATENT DOCUMENTS

| | | | |
|---|---|---|---|
| 2004/0102753 A1* | 5/2004 | Butler | A61F 13/471 604/385.01 |
| 2011/0015604 A1 | 6/2011 | Back | |
| 2012/0308787 A1 | 12/2012 | Kozee et al. | |
| 2016/0008188 A1 | 1/2016 | Lumaque-Steeman | |
| 2016/0278991 A1* | 9/2016 | Lumaque-Steeman | A61F 13/471 |
| 2016/0367411 A1* | 12/2016 | Justiz | A61F 13/5611 |
| 2017/0165100 A1 | 6/2017 | Jackson | |
| 2017/0202714 A1 | 7/2017 | Hurwitz et al. | |

* cited by examiner

WEARABLE ARTICLE FOR URINARY MALE INCONTINENCE

BACKGROUND OF THE INVENTION

Prostate cancer treatment frequently results in some levels of incontinence. With the increased use of early prostate detection tests (e.g., Prostate-Specific Antigen [PSA] blood test) more males are treated at an early age, often beginning in their late 40s. The American Cancer Society estimates that about 286,480 new cases of prostate cancer will be diagnosed in 2022, of which about 40%, or 107,396, are males under 65 years old. As a result, there is a growing number of males that require products to control problems associated with incontinence while at the same time allowing the male to continue with his normal activities. The subject invention relates to a wearable article for use by a male individual that operates to absorb urine. Articles have been developed for treating male incontinence and are typically formed from a plurality of layers or sheets that together operate to collect urine and prevent the collected urine from leaking out of the article. While such articles are effective for individuals having limited mobility, such as an individual confined to a bed or a chair, they either don't provide urine absorption all around the male member or are relatively thick, making it uncomfortable, prone to embarrassing leakage accidents, or encumbering for an individual having extensive mobility.

One type of article for use by a male individual to absorb urine is in the form of underwear having a front portion and a back portion that are connected together forming openings to the individual's legs. Such articles also include an elastic band along the top of the front portion and the back portion for securing the article around the waist of the individual and along the openings for accommodating the individual's legs and reducing leakage of urine. The front portion is formed from a plurality of layers or sheets and are pressed against the male member and operate to absorb urine. Such articles, while effective for absorbing a substantial amount of urine, will allow some urine to remain in contact with the skin of the individual that can cause skin irritation and can be uncomfortable for the individual over time. Further such articles make it difficult for the male to use a urinal without having to lower his pants.

Another type of article for use by a male individual that operates to absorb urine includes a plurality of layers or sheets attached together in such a manner that they form a pocket having an opening whereby a male member is inserted through the opening and extends into the formed pocket. The article is then wrapped around the male member such that any urine is absorbed by one or more of the layers or sheets and is prevented from leaking out of the article. Another type of article used by a male individual that operates to absorb urine includes a plurality of sheets or layers attached together having an opening for receiving a male member. Once the male member extends through the opening, the article is wrapped around the male member such that any urine is absorbed by one or more of the plurality of sheets or layers and urine is prevented from leaking out of the article. While such articles are efficient for absorbing urine and are beneficial for individuals having limited mobility, one problem associated with such articles is that by wrapping the article around the male member it becomes relatively thick, making it difficult or awkward to wear under pants. In addition, by wrapping the plurality of layers or sheets around the male member also makes it difficult or awkward for the individual to urinate in a urinal or toilet, requiring the individual to unwrap the male member to urinate and to re-wrap the male member after urinating.

Another type of article used by a male individual that operates to absorb urine is shown and described in U.S. Pat. No. 6,129,719. As shown, a urine absorbent pad is folded along a traverse center folding line extending across the full width of the absorbent pad, dividing the pad into upper and lower halves. The upper half includes an opening for receiving a male member and the lower section is folded upwardly such that the male member extends in a downward direction sandwiched between the upper and lower halves. The fold line is always away from the male member opening in order to close the bottom side of the bag-shaped article. One problem associated with such a pad is that the position of the male member extending downwardly results in the pad being more noticeable when worn and is also more uncomfortable for the user. Further, the downward direction of the male member will often result in more leakage of urine from the male member. The intended users of this article are bedridden or incontinent men who may leak relatively large amounts of urine and who are not concerned with being able to use urinals.

Accordingly, it would be desirable to have an article that is effective for absorbing urine, that prevents urine from contacting the individual's abdomen area, that is relatively thin such that it can be easily worn under the pants of the individual, that is relatively comfortable for the wearer, reduces leakage or urine from the male member, and allows the individual to easily release the male member for urinating in a urinal or toilet and to easily place the male member back in position in the article.

SUMMARY OF THE INVENTION

The subject invention is a wearable article for urinary male incontinence that is effective for absorbing urine, that prevents or minimizes the likelihood that urine will contact the skin around the wearer's abdomen, that is relatively thin such that it is not apparent when worn under the pants of the individual and can be comfortably worn under the pants of the wearer, that reduces the likelihood of leakage of urine from the male member, and that allows the wearer to easily release the male member for urinating in a urinal or toilet and to easily place the male member back in position in the article.

In a preferred embodiment of the invention, the article comprises a geometrically shaped pad having opposed traversing (horizontal) extending parallel sides and opposed longitudinally (vertical) extending parallel sides. The pad includes an inner sheet formed from an inner liquid permeable material having an inner surface and an outer sheet formed from an outer liquid impermeable material having an outer surface. A liquid absorbent layer is positioned between the inner sheet and the outer sheet. An opening extends through the geometrically shaped pad and is positioned such that the center of the opening is located at the center of the pad. The pad further includes a fold line that always runs through the center of the opening, extends between the opposed longitudinally extending parallel sides and passes through the center of the opening, allowing the pad to be easily folded along the fold line.

In another preferred embodiment of the invention the article comprises a geometrically shaped pad having opposed traversing extending parallel sides and opposed longitudinally extending parallel sides. The pad includes an upper section and an equally sized lower section divided by a center line, an inner sheet formed from an inner liquid permeable material having an inner surface and the outer sheet formed from a liquid impermeable material having an outer surface. A liquid absorbent layer is positioned between the inner sheet and the outer sheet. An opening extends through the pad and is positioned such that the center of the opening is offset upwardly or downwardly from the center line. The pad further includes a fold line that extends from the opposed longitudinally extending parallel sides and always passes through the center of the opening and operates to allow the pad to be easily folded along the fold line.

In another preferred embodiment of the invention, the opening includes one or more cuts or slits extending radially outwardly from the opening and operate to allow the opening to expand and accommodate various sizes of male members.

In another preferred embodiment of the invention, the pad includes a center section positioned between the upper section and the lower section, wherein the thickness of the pad along the center section is smaller (thinner) than the thickness of the pad along the upper section and the lower section.

In another preferred embodiment of the invention, the liquid absorbent layer comprises a fluid absorbent component that operates as an encapsulating medium, for containing a superabsorbent polymer (SAP) absorbent component.

In another preferred embodiment of the invention, the SAP absorbent component is formed from one or more SAPs.

In another preferred embodiment of the invention, the SAP absorbent component is formed from one or more SAPs slush powders, hydrogels, or other such materials that operate to absorb and retain urine.

In another preferred embodiment of the invention, the liquid absorbent layer includes channels effective for distributing urine across and through the liquid absorbent layer.

In another preferred embodiment of the invention, the liquid absorbent layer includes channels having wicking material for distributing urine from the inner sheet along and through the liquid absorbent layer.

In another preferred embodiment of the invention, the liquid absorbent layer includes areas having increased thickness in the form of mounds.

In another preferred embodiment of the invention, the liquid absorbent layer includes mounds formed from urine absorbent material.

A variety of other features and embodiments will be apparent to one skilled in the art from the following description, the figures, and the claims.

BRIEF DESCRIPTION OF THE DRAWINGS

To provide a more complete understanding of the present invention and further features and advantages thereof, reference is now made to the following description taken in conjunction with the accompanying drawings, in which.

DETAILED DESCRIPTION OF THE INVENTION

Figure 1:
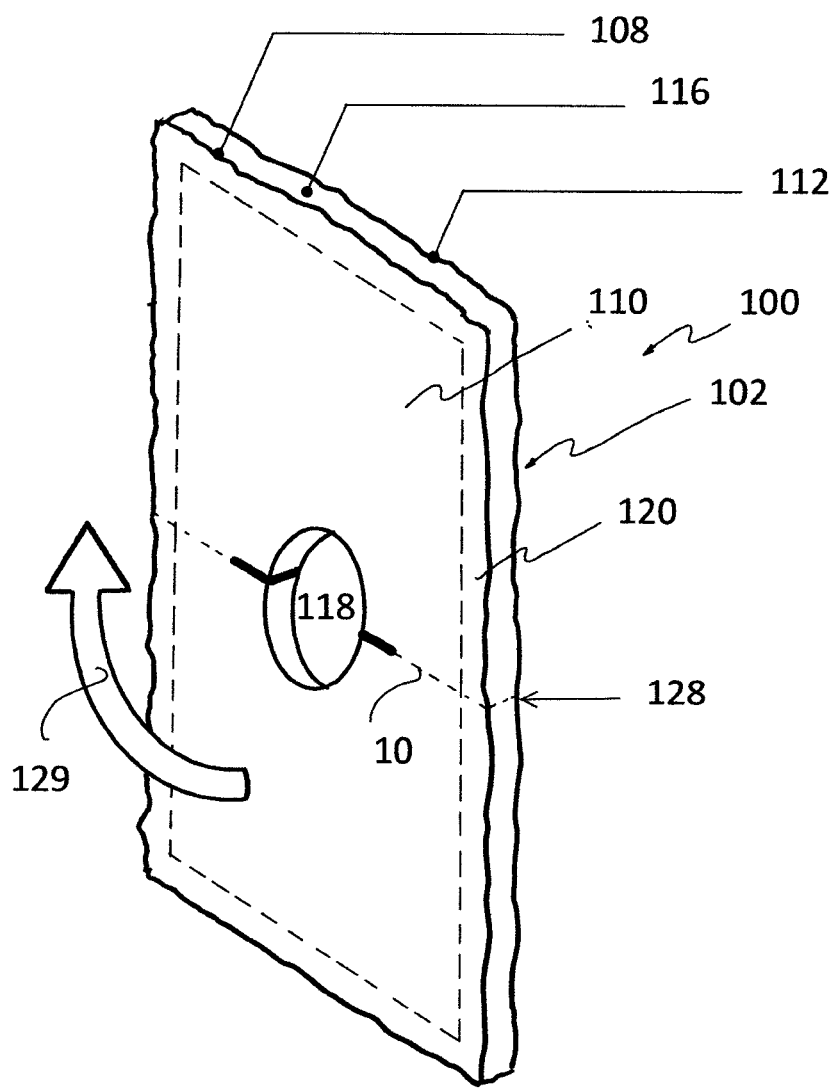
FIG. 1 is a perspective schematic illustration of a preferred embodiment of the wearable article for urinary male incontinence of the subject invention showing a geometrical shaped pad with an inner sheet formed from an inner liquid permeable material having an inner surface, an outer sheet formed from an outer liquid impermeable material having an outer surface, a liquid absorbent layer is positioned between the inner sheet and the outer sheet, and a centrally positioned opening extending through the geometrically shaped pad.
Figure 2:
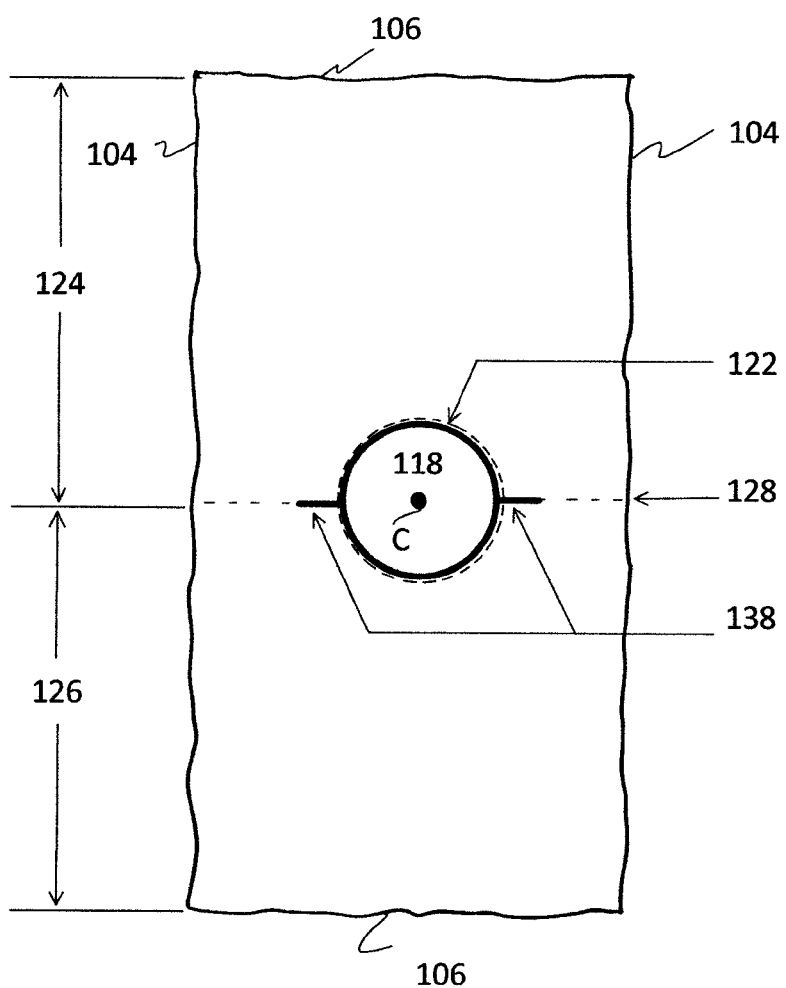
FIG. 2 is a schematic illustration of the wearable article for urinary male incontinence of FIG. 1 showing the inner surface, the opening positioned such that the center of the opening is located at the center of the pad, and a fold line that extends horizontally along the inner surface between the spaced apart opposed longitudinally extending parallel sides of the pad through the center of the opening such that the pad can be folded along the fold line.
Figure 4:
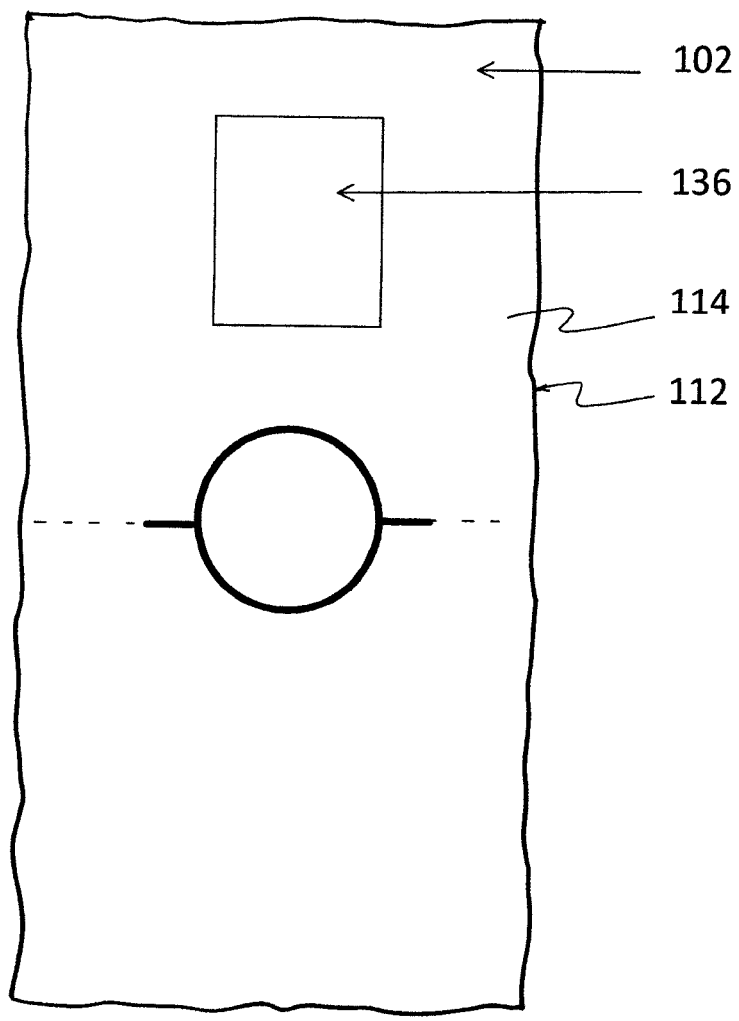
FIG. 4 is a schematic illustration of the wearable article for urinary male incontinence showing the outer surface of the outer sheet having an attachment mechanism for attaching the upper half of the pad to the wearer.

Referring to FIGS. 1 and 2, a wearable article 100 for urinary male incontinence of the subject invention is shown having a geometrically shaped pad 102, such as a generally rectangular shape, formed having two opposed longitudinally extending (vertical) parallel sides 104 and two opposed parallel traversing (horizontal) sides 106. The pad 102 includes an inner sheet 108 formed from an inner liquid permeable material having an inner surface 110, and an outer sheet 112 formed from a liquid impermeable material having an outer surface 114 (FIG. 4). A liquid absorbent layer 116 is positioned between the inner sheet 108 and the outer sheet 112. In a preferred embodiment, as illustrated in FIGS. 1 and 2, a centrally positioned opening 118 extends through the pad 102 and is positioned so that the center C of the opening 118 is located at the center of the pad 102. The inner sheet 108 and the outer sheet 112 are secured together along their outer periphery 120 by gluing, heating, or ultrasonic welding such that the absorbent layer 116 is sandwiched between the inner sheet 108 and the outer sheet 112 thereby forming a unitary pad 102. The various layers are formed from flexible materials and sized to allow the pad to be folded upward in the direction 129. Preferably, the inner sheet 108 and the outer sheet 112 are also joined along the periphery 122 of the opening 118 so that the liquid absorbent layer 116 is sealed along the periphery 122 of the opening 118, thereby preventing urine from escaping outwardly along the periphery 122 of the opening 118. It will be understood that subject invention is not limited to the preceding embodiments, benefits and advantages, and that other embodiments, benefits and advantages of the invention will be apparent and described in the following description, the accompanying drawings, and the appended claims.

As used herein the terms "longitudinal" and "longitudinally" refer to the direction generally perpendicular to the ground when the wearer is standing and is generally parallel to the maximum linear direction of the pad and the term "traverse" refers to the direction perpendicular to the longitudinal direction; the terms "upward" and "upwardly" as used herein refer to the direction away from the feet of the wearer (when standing) and the terms "downward" and "downwardly" as used herein refer to the direction towards the feet of the wearer (when standing); the term "lower" as used herein refers to a position closer to the wearer's feet (when standing); the term "upper" refers to a position farther away from the wearer's feet (when standing); the term "vertical" refers to the longitudinal direction; and the term "horizontal" refers to the traverse direction (generally perpendicular to the vertical direction).

The liquid absorbent layer 116 is preferably made from absorbent material components typically used in diapers, such as a fibrous material (for example wood pulp and cotton fibers) and synthetic polymers (for example a hydrophilic polymer). Synthetic polymers can also include fine particles of an acrylic acid derivative, such as sodium acrylate, potassium acrylate, or an alkyl acrylate, or can be formed from or include super absorbent polymers or slush powders, hydrogels, or other super-absorbent material components (collectively referred to as SAP material components) enclosed within the fibrous material components that operates to absorb and retain urine. The inner sheet 108 may be perforated or non-perforated nonwoven fabric or a porous plastic. Such materials are typically liquid permeable materials that are used in diapers, such as a nonwoven fabric formed from plastic resins (for example, nylon, polyester, polyethylene, or polypropylene having interlocking plastic fibers). The outer sheet 112 is preferably formed from liquid impermeable materials typically used in diapers such as a nonwoven fabric (for example plastic resins made from nylon, polyester, polyethylene, or polypropylene). In a preferred embodiment of the invention, the outer sheet may be formed from a material that is impervious to liquid but is breathable such that vapors can escape.

Figure 3:
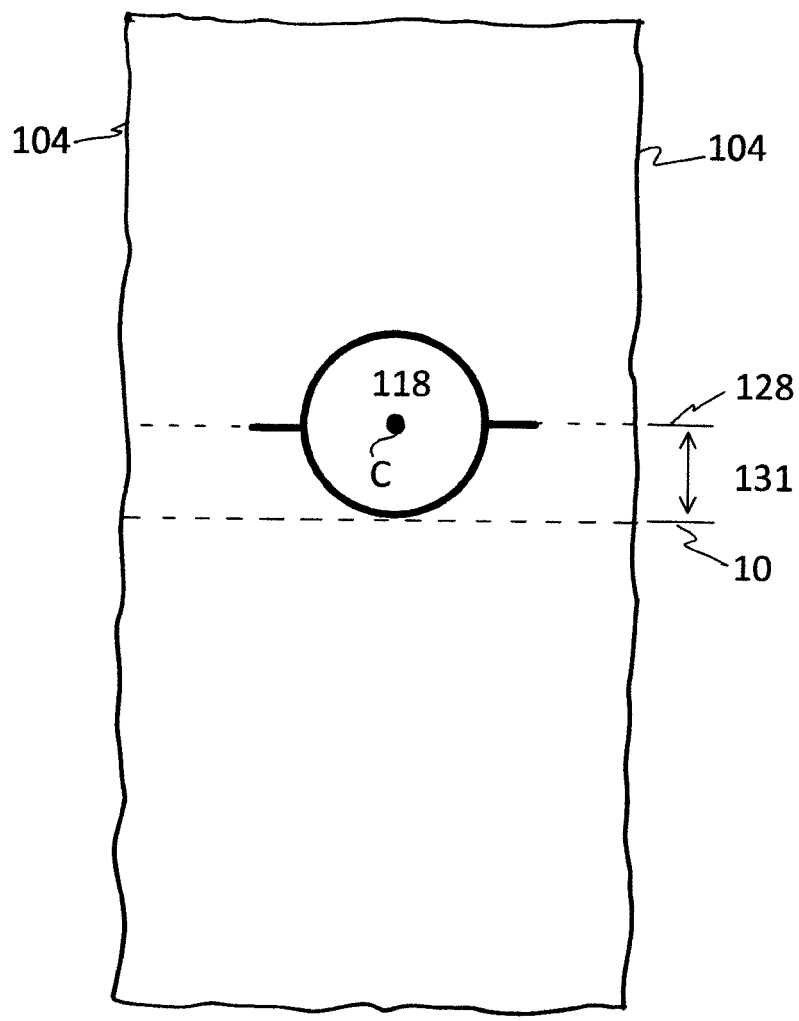
FIG. 3 is a schematic illustration of another preferred embodiment of the invention showing the center of the opening positioned equal distance from the opposed longitudinally extending parallel sides but upwardly or downwardly from the horizontal centerline of the pad, a fold line extends horizontally across the pad from the two opposed longitudinally extending parallel sides through the center of the opening such that the pad can be folded along the fold line.
Figure 11:
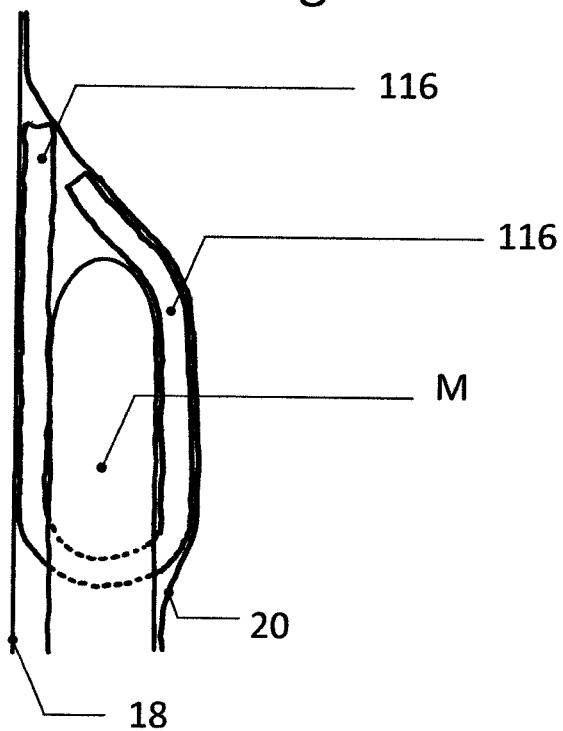
FIG. 11 is a schematic cross-sectional illustration taken along cross-section 11-11 of FIG. 10 showing a male member inserted through the opening and the pad which is folded along the fold line such that the inner surface of the lower section is positioned along the inner surface of the upper section and wherein the male member is positioned between the lower section and the upper section.

In a preferred embodiment of the invention, as illustrated in FIGS. 1 and 2, the liquid permeable inner sheet 108 includes an upper section 124 and a lower section 126 separated along the horizontal centerline 10 of the pad 102. A fold line 128 extends horizontally across the pad 102 from the two opposed longitudinally extending parallel sides 104 and is equally spaced from the two opposed parallel traversing (horizontal) sides 106 such that the fold line 128 runs along the horizontal center line 10 and through the center C of the opening 118. Thus, when positioned on the wearer, folding the pad 102 along the fold line 128 operates to allow the lower section 126 to be moved upwardly such that the inner surface 110 of the inner sheet 108 is positioned along the lower section 126 and parallel to the inner surface 110 of the inner sheet 108 along the upper section 124. Thus, in this preferred embodiment, the fold line 128 is also the horizontal centerline 10 of the pad 102. In another preferred embodiment of the invention, as illustrated in FIG. 3, the opening 118 is positioned at offset 131 from the horizontal centerline 10 of the pad 102. As shown, the center C or the opening 118 is positioned such that it is equal distance from the two opposed longitudinally (vertical) extending parallel sides 104 but upwardly from the horizontal centerline 10 of the pad 102. A fold line 128 extends horizontally across the pad 102 from the two opposed longitudinally (vertical) extending parallel sides 104 running through the center C of the opening 118. Thus, in this preferred embodiment, the fold line 128 is positioned parallel to and upwardly from the horizontal centerline 10 of the pad 102. It should be apparent that by positioning the fold line such that it always runs through the center of the opening, unlike previously designed pads, permits the male member to be positioned, when the pad is folded, in a vertical upward position such that the inner surfaces of the lower section and the upper section are closer together reducing the overall folded thickness of the pad and the likelihood of the wearing of the pad to be noticeable. Further, by positioning the male member such that it is positioned in an upward vertical position operates to create a bend the urethra that reduces urine flow pressure and potential leakage of urine out of the male member. It should also now be apparent, as illustrated in FIG. 11, that the location of the opening slightly offset from the middle of the pad results that when the pad is folded, the horizontal top surface 106 of the upper section 124 not lining up with the horizontal top surface 106 of the lower section 126 (unequal height folds). Such differences in the vertical positions of the horizontal top surfaces 106 operate to help the wearer separate the sections to unfold the pad when using a urinal. Accordingly, if the wearer needs to use a urinal, the wearer can easily grip upper end of the lower section between his thumb and finger and lower (unfold) the lower section allowing the male member to be in position to use the urinal. The lower section can then be moved upwardly (fold) back into position parallel to the upper section. Thus, when the article is positioned on the wearer, the lower section of the pad can fold easily downwardly allowing the male member to easily urinate in a urinal and then the lower section can easily fold upwardly fold back into its wearing position. It should also be apparent that by locating the opening and fold line vertically offset from the horizontal center line of the pad further improves the ability and ease for the wearer in using the urinal.

In another preferred embodiment of the invention, as illustrated in FIG. 4, the outer surface 114 of the outer sheet 112 includes a pad attachment mechanism 136, such as a releasable tape, that attaches to the wearer to help maintain upper half of the pad in place when being worn and can be easily detached from the wearer.

In a preferred embodiment, as illustrated in FIG. 2, extending radially outwardly from the opening 118 are slots 138 that operate to allow the opening 118 to more easily accommodate different size male members, such as a larger male member while allowing the opening 118 to maintain close contact with smaller male members thereby minimizing the likelihood of urine leakage around the male member and the opening.

Figure 5:
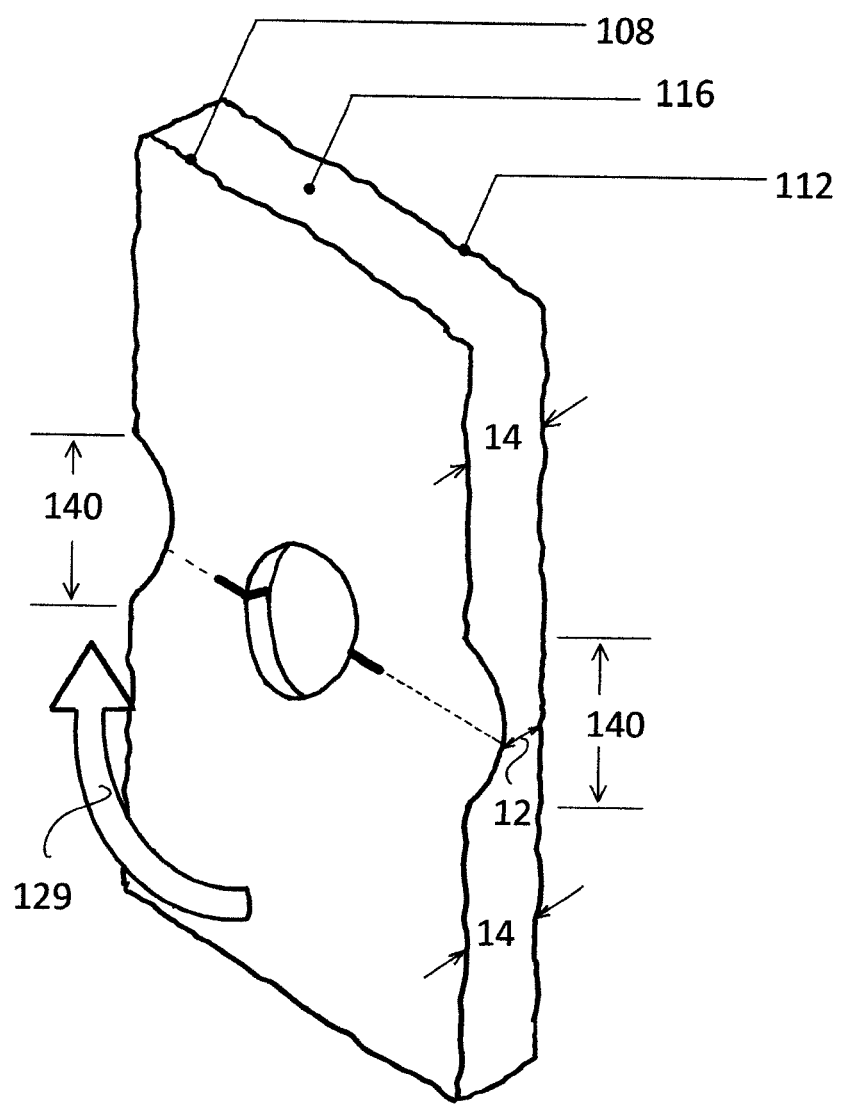
FIG. 5 is a schematic perspective illustration of another preferred embodiment of the invention showing the pad having a center section positioned between an upper section and a lower section, wherein the thickness of the pad along the center section is smaller than the thickness of the pad along the upper section and the lower section.

In another preferred embodiment of the invention, the pad includes a middle section 140 positioned between the upper section 124 and the lower section 126 such that the horizontal center line 10 runs along the middle section dividing the middle section 140 horizontally in half. As illustrated in FIG. 5, the thickness 12 of the pad along the middle section 140 is smaller than the thickness 14 of the pad along the upper section 124 and the lower section 126. It should now be apparent to one skilled in the art that by reducing and preferably minimizing the thickness of the pad along the middle section permits a thicker (i.e., with more absorbency) pad to be easily folded along the fold line in an upward direction 129. It should be understood that the thickness of the pad, as well as the type of absorbing material, can be selected based on the particular need of the wearer.

In another preferred embodiment of the invention, the inner sheet 108 is formed from permeable or a semi-permeable material that operate to permit urine to flow from wetted inner surface 110 through the inner sheet 108 to be absorbed in the liquid absorbent layer 116. The inner sheet 108 operates to distribute urine such that it distributes the urine across the liquid absorbent layer 116 thereby increasing the absorption rate of the liquid absorbent layer 116. It should be understood that by distributing the urine across the liquid absorbent layer allows the liquid absorbent layer (thus the pad) to be thinner in thickness. In a preferred embodiment of the invention, the liquid absorbent layer 116 is formed from one or more liquid absorbent components 142, such as a spun bond non-woven material made from long fibers, bonded together by chemical, mechanical, heat or solvent treatment. Such liquid absorbent components 142 operate to draw urine from the inner sheet 110 and distributes the urine across the liquid absorbent layer 116, such as by wicking or capillary action, that stores the urine. In a preferred embodiment, the liquid absorbent layer 116 includes a spun bond woven liquid absorbent component 142 such as polyester, including, but not limited to Rayon, polypropylene, polyethylene terephthalate (PET) or a combination thereof and has SAP liquid absorbent components 144 within the liquid absorbent layer structure.

Figure 6:
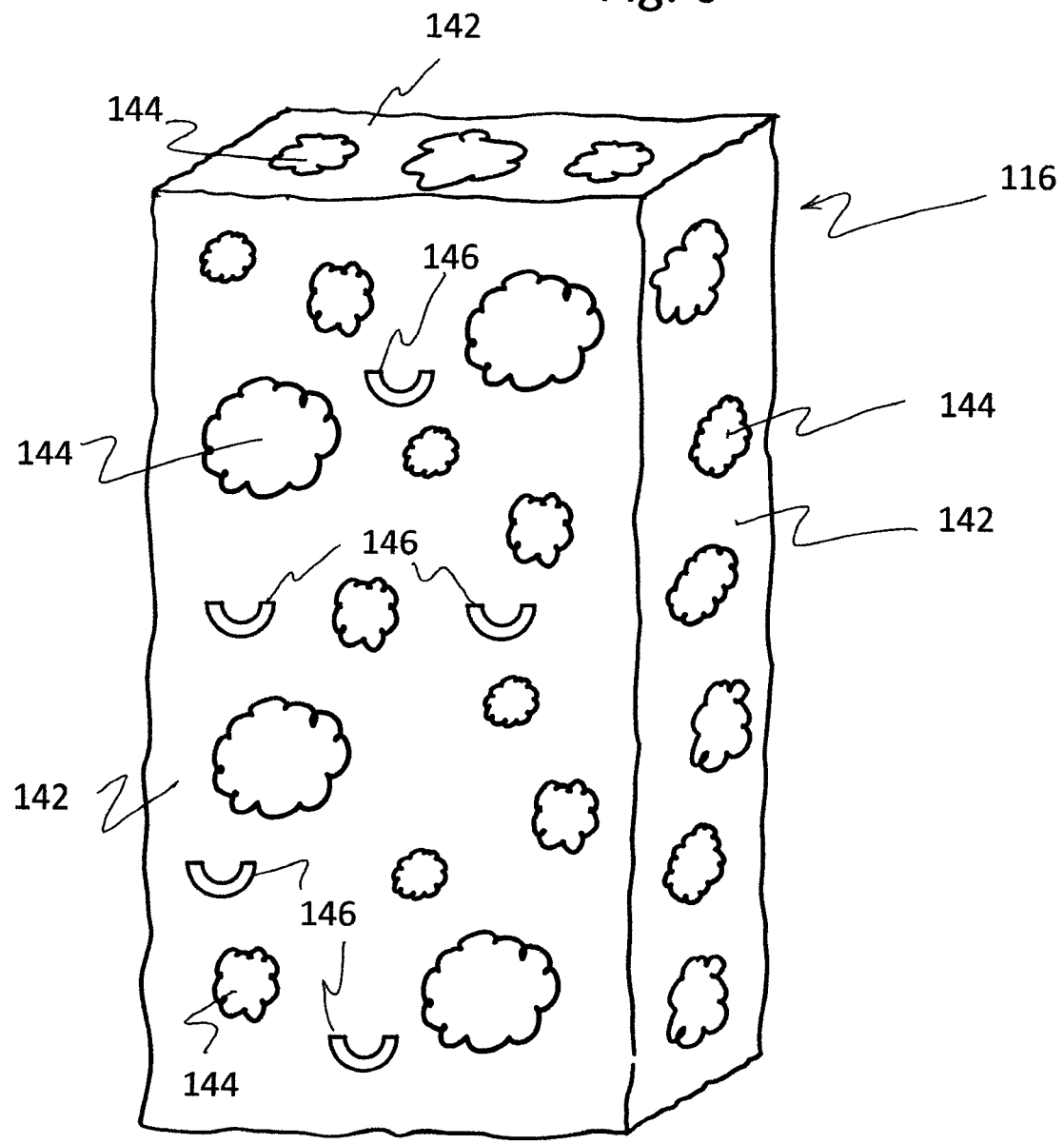
FIG. 6 is a schematic illustration showing the inner sheet, the outer sheet and the liquid absorbent layer in between, the liquid absorbent layer having a plurality of channels and absorbent components and/or SAP absorbent components therein.
Figure 7:
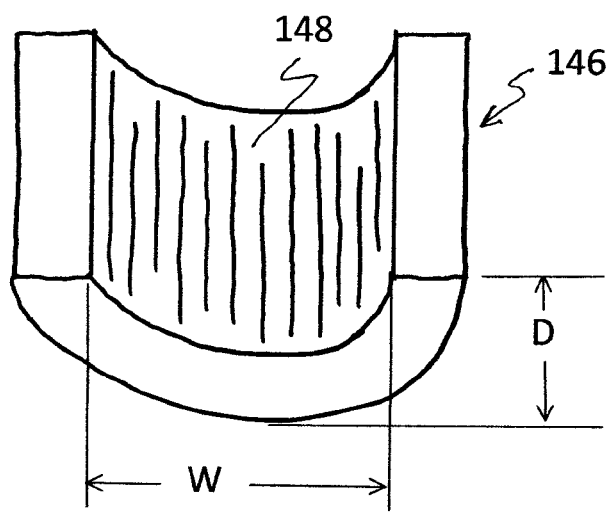
FIG. 7 is a schematic perspective illustration of a channel of FIG. 6 showing the length, width, and depth of the channel and showing wicking material contained within the channel.

As illustrated in FIGS. 6 and 7, in a preferred embodiment of the invention, the liquid absorbent layer 116 further includes one or more channels 146 that operate to direct urine from the inner sheet 108 through the liquid absorbent layer 116, such that the urine is distributed along and through the liquid absorbent layer 116 so that the urine comes into direct contact with the liquid absorbent components 142 and/or the SAP liquid absorbent components 144 within the liquid absorbent layer 116. It should be understood that the rate of the absorption of the urine is determined by the number and the area (defined by the length L, width W and the depth D of the channels), as illustrated in FIG. 7, and the number of the liquid absorbing components 142 and 144. It should also be understood that the rate of urine absorption of the one or more liquid absorbent components can also be determined by the geometric shape of the perimeters of the liquid absorbing components. For example, increasing the surface area of the one or more liquid absorbent components increases the rate of liquid absorption of the one or more liquid absorbent components. Further, it should be understood that changing the sizes (surface area) and number of the channels, can increase the flow and the absorption rate of the urine and can also operate to distribute the urine through and across the liquid absorbing layer to increase the efficiency of the pad and its ability to capture urine and minimize the likelihood of urine leakage out of the pad. Further, increasing the absorption efficiency (such as by distributing the urine across the liquid absorbing layer) minimizes the thickness of the liquid absorbent layer. Thus, by controlling the distribution of the urine allows the liquid absorbent layer to be thinner in thickness, making the pad less conspicuous when used and increases the time period before the pad needs to be replaced.

In another preferred embodiment, as shown in FIG. 7, the one or more channels 146 include channel wicking material 148 having hydrophobic properties positioned within the channels 146 that operates to guide urine through the channels 146, such as by wicking or capillary action, to the liquid absorbent layer 116 for absorption by the liquid absorbent components 142. As shown, the channel wicking material 148 operates to draw urine from the inner sheet 108 for absorption by the liquid absorbent layer 116. In a preferred embodiment of the invention, the channel wicking material 148 is formed from a wet-laid cellulose pulp material, preferably comprising soft wood pulp having fibers of sufficient length to provide the necessary wicking of the hydrating fluid to distribute urine through the one or more channels 146 and along the surfaces of the one or more liquid absorbent components 142 and 144. Preferably, the fiber length of the distributing wicking layer is optimized to maximize the capillary or wicking characteristics of the distributing wicking material. In a preferred embodiment of the invention, the distributing wicking material is spun-laced fabric made from a combination of cellulosic fibers, including, but not limited to, Viscose rayon or lyocell, and synthetic fibers such as, but not limited to, polyester fibers.

Figure 8:
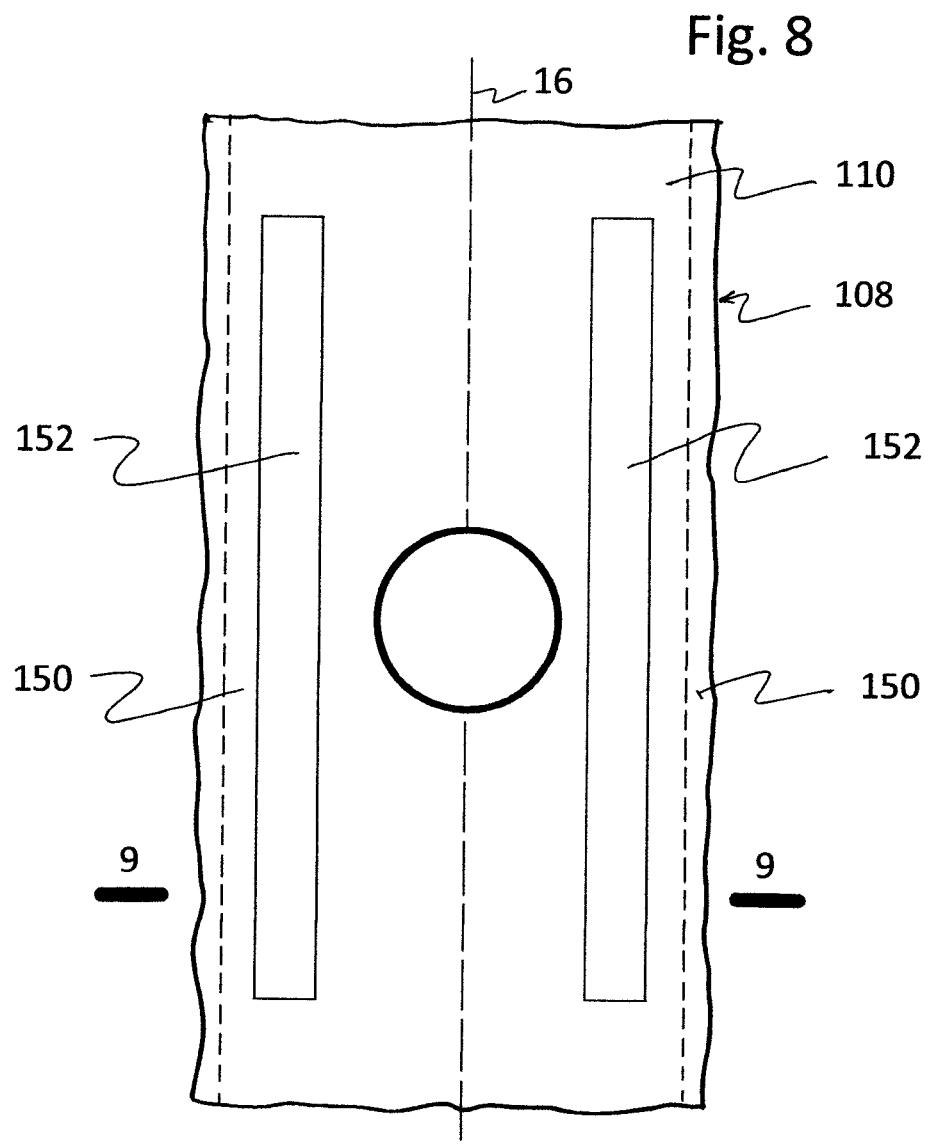
FIG. 8 is a schematic illustration showing the inner surface of the inner sheet showing liquid absorbing mounds.
Figure 9:
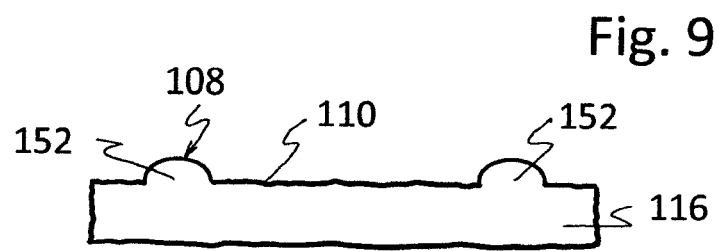
FIG. 9 is a schematic cross-sectional view taken along cross-section 10-10 showing the liquid absorbing mounds of FIG. 8.

In another preferred embodiment of the invention, as illustrated in FIGS. 8 and 9, the liquid absorbent layer 116 includes additional liquid absorbent components 142 and 144 positioned between the longitudinal centerline 16 of the pad 102 and the periphery 150 of the opposed longitudinally extending parallel side walls 104 forming opposed parallel longitudinally extending liquid absorbing mounds 152. The longitudinally extending mounds 152 operate to absorb urine and reduce the likelihood of urine leaking through the open sides of the pad. Further, the mounds also operate to increase the comfort of the pad and reduces the likelihood of the male member dislocating out of the pad.

Figure 10:
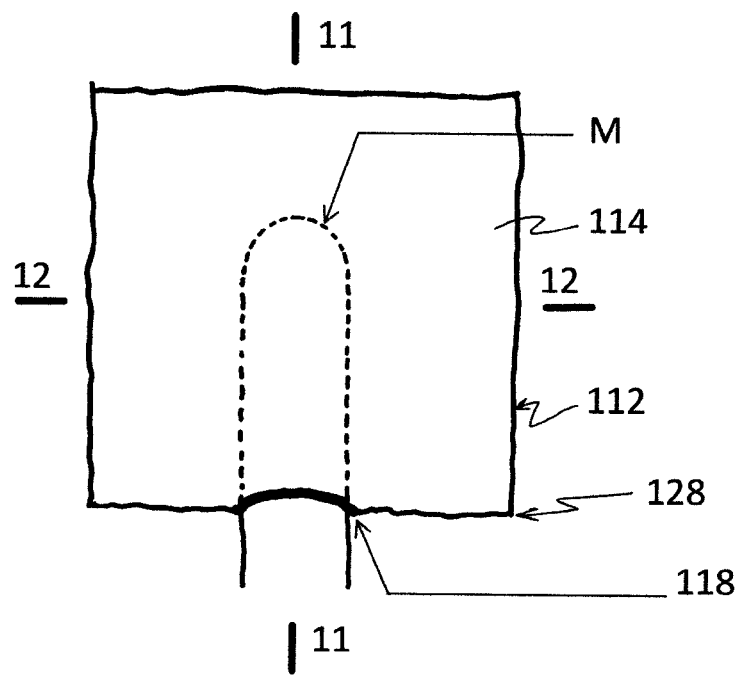
FIG. 10 is a schematic illustration showing the male member inserted through the opening and the lower section of the pad folded along the fold line such that the male member is blanketed by the pad.
Figure 12:
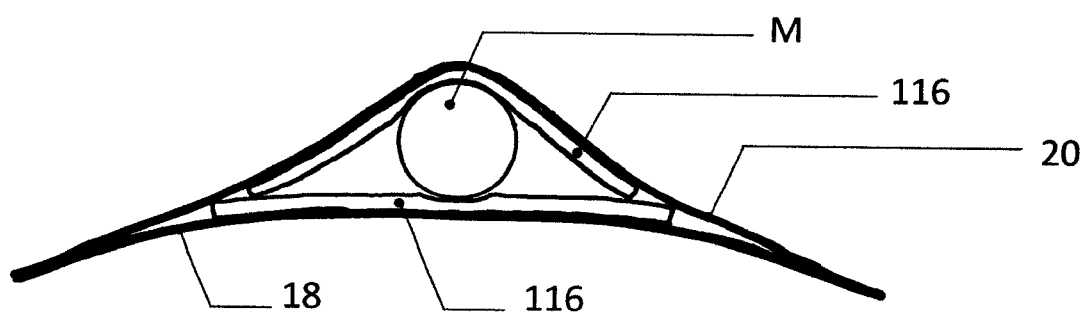
FIG. 12 is a schematic cross-sectional view taken along cross-section 12-12 of FIG. 10 showing the male member inserted through the opening in the pad and positioned between the lower section and the upper section and further showing the upper portion of the outer surface of the outer sheet positioned along the abdomen of the wearer and a lower portion of the outer surface of the outer sheet positioned along the briefs (underwear) of the wearer.
Figure 13:
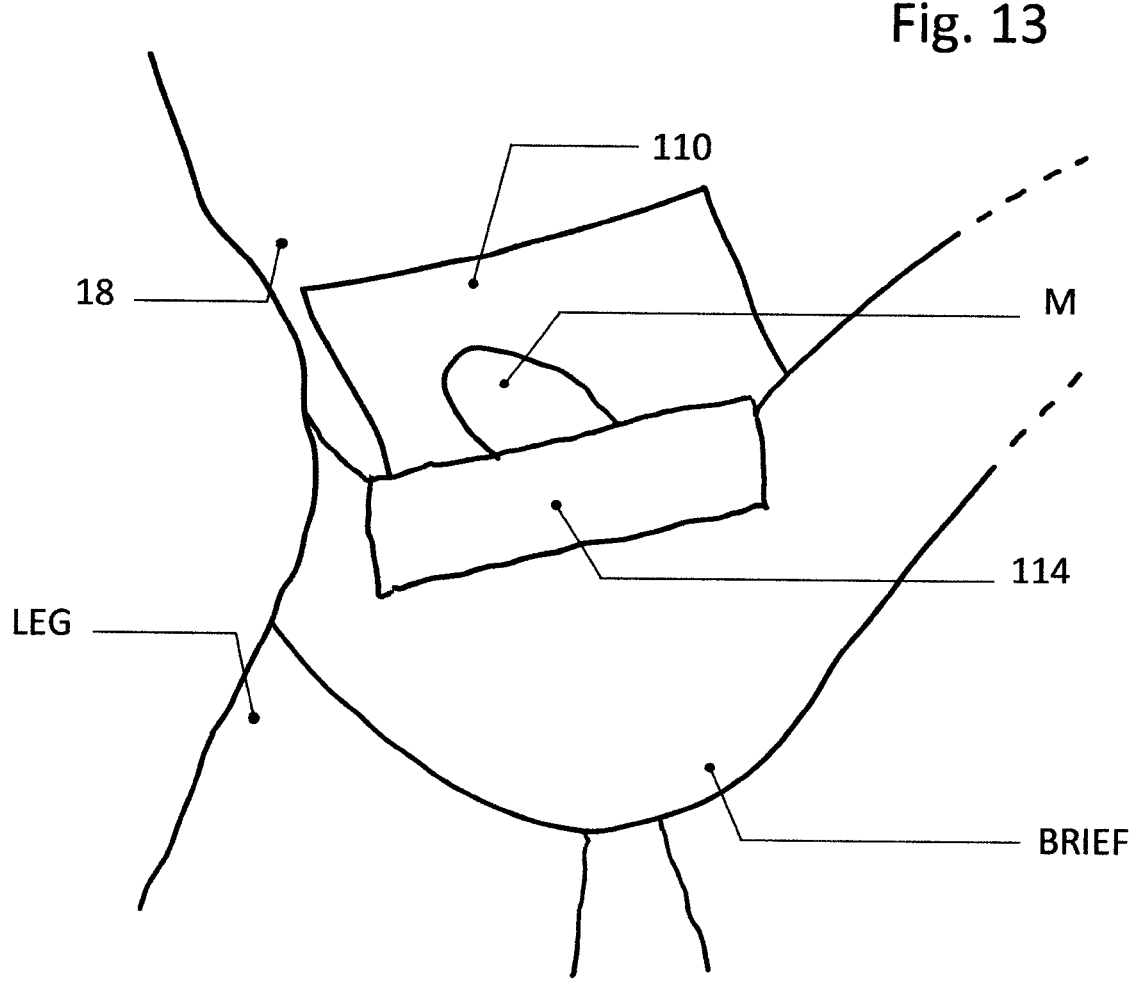
FIG. 13 is a side schematic cross-section view of the wearable article for urinary male incontinence showing the male member positioned between the lower section and the upper section and further showing the upper portion of the outer surface of the outer sheet positioned along the abdomen of the wearer and a lower portion of the outer surface of the outer sheet positioned along the briefs (underwear) of the wearer.

In applying the pad to the wearer, as illustrated in FIGS. 10-12, the outer surface 114 of the outer sheet 112 of the pad 102 is positioned towards the wearer and moved into contact with the wearer along his groin area 18. The male member M is then inserted from the outer surface 114 towards the inner surface 110 through the opening 118. Once the male member M is fully inserted through the opening 118, the pad 102 is then folded upwardly along the fold line 128 into its wearing position such that the inner surface 110 of the inner sheet 108 is positioned along and covers the male member M so that the inner surface 110 of the inner sheet 108 blankets the male member M. In operation, the inner sheet 108 is liquid permeable and operates to permit urine that was discharged from the male member M to flow through the inner surface 110 and be absorbed by and maintained by the liquid absorbent layer 116. The urine that accumulates in the liquid absorbent layer 116 is prevented from leaking out of the pad 102 by the outer sheet 112 formed from a liquid impermeable material. It should now be apparent that by folding the pad 102 along the fold line 128 operates to allow any discharge of urine to be absorbed by the liquid absorbent layer and prevents or reduces the likelihood of urine from contacting the wearer's groin area 14 and the wearer's underwear or pants 20. It should also now be apparent that by folding the pad along the fold line 128 rather than wrapping the layers around the male member minimizes the bulk of the pad, often seen in pads that are wrapped around a male member, making the wearing of the pad less apparent when the wearer is dressed.

The wearable article for urinary male incontinence of the subject invention has a variety of features. For example, the pad operates to substantially absorb urine discharge from the wearer. Further, the article of the subject invention is relatively thin, thereby the wearer does not feel encumbered and is inconspicuous when worn beneath clothing, such as pants and shorts. In addition, the article can be easily placed in position of the wearer and allows the wearer to use a urinal with little difficulty. It should also be apparent that the insertion of the male member through the opening positions the male member into a general vertical position when the pad is folded which operates to create a bend the urethra that reduces urine flow pressure and potential leakage. Further, the placement of the male member between the mounds and/or the longitudinally extending hollow portion operates to limit movement of the male member to the left or right thereby minimizing the potential of leakage along the sides of the pad.

It should now be apparent that the subject invention provides a wearable article for urinary male incontinence that is effective for absorbing urine, that prevents or minimizes the likelihood that urine will contact the skin around the wearer's abdomen, that is relatively thin such that it is not apparent when worn under the pants of the individual and can be comfortably worn under the pants of the wearer, and allows the wearer to easily release the male member for urinating in a urinal or toilet and to easily place the male member back in position in the article.

The invention claimed is:

1. A wearable article for absorbing urine and preventing or reducing the likelihood of urine contacting a wearer's abdomen and a wearer's underwear or pants caused by urinary male incontinence, the wearable article comprising:
   a geometrically shaped pad having opposed traversing extending parallel sides and opposed longitudinally extending parallel sides and having an upper section and a lower section;
   wherein said geometrically shaped pad comprises:
   an inner sheet formed from a permeable material having an inner surface;
   an outer sheet formed from an outer impermeable material having an outer surface;
   an absorbent layer is positioned between said inner sheet and said outer sheet;
   an opening having a center extending through said pad for receiving a male member; and
   a traversing extending fold line that extends between said opposed longitudinally extending parallel sides and passes through said center of said opening and whereby said pad is folded along said fold line;
   wherein when said pad is folded along said fold line, said outer sheet has an outer surface for positioning along the wearer's abdomen and for positioning along the wearer's briefs or pants;
   wherein when said pad is folded along said fold line, said opposed traversing extending parallel sides are parallel to each and to said fold line and said longitudinally extending parallel sides are parallel to each other; and
   wherein when said pad is positioned along the wearer's abdomen and the male member is received in said opening, the male member is positioned in an upward vertical direction when the wearer is standing.

2. The wearable article of claim 1, wherein said opening includes two opposed cuts or slits extending radially outwardly from said opening along said fold line effective for expanding said opening to accommodate various sizes of male members.

3. The wearable article of claim 1, wherein said absorbent layer comprises an absorbent component that is an encapsulating medium for containing superabsorbent polymers (SAPs) absorbent components.

4. The wearable article of claim 1, wherein said absorbent layer includes one or more liquid absorbent components formed from a material effective for distributing urine across said absorbent layer by wicking or capillary action and wherein said absorbent layer further includes channels effective for directing urine from said inner sheet through said absorbent layer so that the urine comes into direct contact with said liquid absorbent component.

5. The wearable article of claim 1, wherein said absorbent layer includes channels having wicking material within said channels that distribute urine from said inner sheet along and through said absorbent layer.

6. The wearable article of claim 1, wherein said absorbent layer includes longitudinally extending mounds that absorb urine and reduce urine leakage along said opposed longitudinally extending sides when the pad is positioned on the wearer.

7. A wearable article for urinary male incontinence comprising:
   a geometrically shaped pad having opposed traversing extending parallel sides and opposed longitudinally extending parallel sides and having an upper section and a lower section;
   wherein said geometrically shaped pad comprises:
   an inner sheet formed from a permeable material having an inner surface;
   an outer sheet formed from an outer impermeable material having an outer surface;
   an absorbent layer positioned between said inner sheet and said outer sheet;
   an opening having a center extending through said pad; and
   a middle section having a traversing extending fold line that extends between said opposed longitudinally extending parallel sides and passes through said center of said opening and whereby said pad is folded along said fold line;
   wherein said middle section is positioned between said upper section and said lower section, wherein said upper section has a thickness and said lower section has a thickness wherein said middle section has a thickness that is smaller (thinner) than said thickness of said upper section and said lower section;

wherein when said pad is folded along said fold line, said opposed traversing extending parallel sides are parallel to each other and to said fold line and said opposed longitudinally extending parallel sides are parallel to each other; and wherein when said pad is positioned on the wearer and folded along said fold line, and said outer sheet along said upper section is positioned along the wearer's abdomen and said lower section is positioned along the wearer's briefs or pants, when the male member is received in said opening, the male member is positioned in an upward vertical direction when the wearer is standing.

8. The wearable article for urinary male incontinence of claim 7, wherein said opening includes two opposed cuts or slits extending radially outwardly from said opening along said fold line effective for expanding said opening to accommodate various sizes of male members.

9. The wearable article for urinary male incontinence of claim 7, wherein said absorbent layer comprises an absorbent component that is an encapsulating medium for containing superabsorbent polymers (SAPs) absorbent components.

10. The wearable article for urinary male incontinence of claim 7, wherein said absorbent layer includes one or more liquid absorbent components formed from a material effective for distributing urine across said absorbent layer by wicking or capillary action and wherein said absorbent layer further includes channels effective for directing urine from said inner sheet through said absorbent layer so that the urine comes into direct contact with said liquid absorbent component.

11. The wearable article for urinary male incontinence of claim 7, wherein said absorbent layer includes channels having wicking material within said channels that distribute urine from said inner sheet along and through said absorbent layer.

12. The wearable article for urinary male incontinence of claim 9, wherein said absorbent layer includes parallel longitudinally extending mounds that absorb urine and reduce urine leakage along said opposed longitudinally extending parallel sides when the pad is positioned on the wearer.

13. The wearable article of claim 1, wherein said outer surface of said outer sheet along said upper section includes a pad attachment mechanism for attaching to a wearer's abdomen to maintain the wearable article in place during use.

14. The wearable article of claim 1, wherein the male member has a urethra and when the male member is inserted in said opening the male member is positioned such that a bend is created in the urethra when the pad is folded and placed on the wearer.

15. The wearable article for urinary male incontinence of claim 7, wherein said outer surface of said outer sheet along said upper section includes a pad attachment mechanism for attaching to a wearer's abdomen to maintain the wearable article in place during use.

16. The wearable article for urinary male incontinence of claim 7, wherein said outer surface of said outer sheet along said upper section includes a pad attachment mechanism in the form of a releasable tape for attaching to the wearer's abdomen to maintain the wearable article in place during use.

17. The wearable article of claim 7, wherein the male member has a urethra and when the male member is inserted in said opening the male member is positioned such that a bend is created in the urethra when the pad is folded and placed on the wearer.

18. The wearable article for urinary male incontinence of claim 1, wherein said outer surface of said outer sheet along said upper section includes a pad attachment mechanism in the form of a releasable tape for attaching to the wearer's abdomen to maintain the wearable article in place during use.

19. A method for attaching a wearable article to a wearer for urinary male incontinence comprising the steps of:

attaching a geometrically shaped pad having opposed traversing extending parallel sides and opposed longitudinally extending parallel sides and having an upper section and a lower section, wherein the geometrically shaped pad comprises:

an inner sheet formed from a permeable material having an inner surface;

an outer sheet formed from an outer impermeable material having an outer surface;

an absorbent layer positioned between the inner sheet and the outer sheet;

an opening having a center extending through the pad; and a middle section having a fold line that extends between the opposed longitudinally extending parallel sides and passes through the center of the opening;

inserting the male member through the opening from the said outer surface of said outer sheet such that the male member is positioned in an upward vertical direction when the wearer is standing;

positioning the pad on the wearer such that the outer sheet along the upper section is positioned along the wearer's abdomen and folding the pad along the fold line such the lower section is in position for placement along the wearer's briefs or pants such that the male member is positioned in an upward vertical direction when the wearer is standing; and wherein when said pad is folded along said fold line, said opposed traversing extending parallel sides are parallel to each other and to said fold line and said opposed longitudinally extending parallel sides are parallel to each other.

20. The method for attaching a wearable article to a wearer for urinary male incontinence of claim 19, wherein upon folding the wearable article, when the male member is received in the opening, the upper section and the lower section are directly disposed over one another such that the male member is positioned equally spaced between a single said upper section and a single said lower section.

\* \* \* \* \*